(12) United States Patent
Deane et al.

(10) Patent No.: US 11,110,293 B2
(45) Date of Patent: Sep. 7, 2021

(54) PHOTOTHERAPY SYSTEMS AND METHODS OF PHOTOTHERAPY

(71) Applicant: L'Oreal, Paris (FR)

(72) Inventors: Geoffrey F. Deane, Bellevue, WA (US); Lily Truong, Redmond, WA (US); Zane Bowman Allen Miller, Seattle, WA (US)

(73) Assignee: L'OREAL, Paris (FR)

( * ) Notice: Subject to any disclaimer, the term of this patent is extended or adjusted under 35 U.S.C. 154(b) by 28 days.

(21) Appl. No.: 16/240,585

(22) Filed: Jan. 4, 2019

(65) Prior Publication Data
US 2020/0215350 A1 Jul. 9, 2020

(51) Int. Cl.
*A61N 5/06* (2006.01)

(52) U.S. Cl.
CPC .......... *A61N 5/0616* (2013.01); *A61N 5/0622* (2013.01); *A61N 2005/065* (2013.01); *A61N 2005/0626* (2013.01); *A61N 2005/0662* (2013.01)

(58) Field of Classification Search
CPC .................................................... A61N 5/0622
See application file for complete search history.

(56) References Cited

U.S. PATENT DOCUMENTS

| | | | | |
|---|---|---|---|---|
| 2003/0109906 A1* | 6/2003 | Streeter | ................ | A61N 5/0613 607/88 |
| 2006/0106435 A1* | 5/2006 | Fraval | ................... | A61B 5/444 607/88 |
| 2008/0262574 A1* | 10/2008 | Briefs | ................. | A61N 5/0616 607/88 |
| 2011/0144723 A1* | 6/2011 | Streeter | ............... | A61N 5/0618 607/88 |
| 2012/0035690 A1* | 2/2012 | Turtzo | ..................... | A61F 7/00 607/90 |
| 2012/0148976 A1* | 6/2012 | Brawn | ................ | A61N 5/0613 433/24 |
| 2017/0348506 A1* | 12/2017 | Berman | ................. | H05B 47/19 |
| 2018/0021593 A1* | 1/2018 | Vartanian | ............. | A61N 5/0618 607/90 |
| 2019/0388707 A1* | 12/2019 | Shenfarber | .......... | A61N 5/0622 |

* cited by examiner

*Primary Examiner* — Rex R Holmes
*Assistant Examiner* — Jennifer L Ghand
(74) *Attorney, Agent, or Firm* — Christensen O'Connor Johnson Kindness PLLC

(57) ABSTRACT

Phototherapy systems and methods of phototherapy are described. In an example, the phototherapy system includes a therapeutic light source configured to emit phototherapeutic light towards a subject; and a placebo light source configured to emit placebo light towards the subject. In an embodiment, the light, including the phototherapeutic light and the placebo light, emitted by the phototherapy system is configured to be visually perceived by the subject as continuous light. In an embodiment, the placebo light is a metameric match of the phototherapeutic light. In an embodiment, the method includes emitting the placebo light in a wavelength range and at an intensity configured to be visually perceived by the user as the phototherapeutic light, such as where the placebo light is a metameric match of the phototherapeutic light.

6 Claims, 3 Drawing Sheets

PHOTOTHERAPY SYSTEMS AND METHODS OF PHOTOTHERAPY

SUMMARY

In one aspect, the present disclosure provides a phototherapy system generally including a therapeutic light source configured to emit phototherapeutic light towards a subject; a placebo light source configured to emit placebo light towards the subject; and a controller operatively coupled to the therapeutic light source and the placebo light source, the controller including instructions that, when executed by the controller, cause the phototherapy system to perform operations including emitting the phototherapeutic light from the therapeutic light source; and emitting the placebo light from the placebo light source, wherein the phototherapy system is configured to emit light, including the phototherapeutic light and the placebo light, that is configured to be visually perceived by the subject as continuous light.

In another aspect, the present disclosure provides a method of phototherapy generally including emitting phototherapeutic light from a phototherapeutic light source onto a portion of a subject; and emitting placebo light from a placebo light source for visual receipt by the subject; wherein combined light including the phototherapeutic light and the placebo light is configured to be perceived by the subject as continuous light.

In accordance with any of the embodiments disclosed herein, the controller includes instructions that, when executed by the controller, cause the phototherapy system to perform operations including emitting phototherapeutic light from the therapeutic light source as a plurality of phototherapeutic light pulses. In accordance with any of the embodiments disclosed herein, the controller includes instructions that, when executed by the controller, cause the phototherapy system to perform operations including emitting placebo light from the placebo light source as a plurality of placebo light pulses. In accordance with any of the embodiments disclosed herein, one or more of the plurality of placebo light pulses are interspersed between phototherapeutic light pulses of the plurality of phototherapeutic light pulses.

In accordance with any of the embodiments disclosed herein, emitting the phototherapeutic light includes emitting a plurality of phototherapeutic light pulses from the phototherapeutic light source. In accordance with any of the embodiments disclosed herein, emitting the placebo light includes emitting a plurality of placebo light pulses from the placebo light source. In accordance with any of the embodiments disclosed herein, one or more of the plurality of placebo light pulses are interspersed between phototherapeutic light pulses of the plurality of phototherapeutic light pulses.

In accordance with any of the embodiments disclosed herein, the controller includes instructions that, when executed by the controller, cause the phototherapy system to perform operations including emitting the placebo light from the placebo light source in a wavelength range and at an intensity configured to be visually perceived by the user as the phototherapeutic light.

In accordance with any of the embodiments disclosed herein, emitting the placebo light with the placebo light source includes emitting placebo light in a wavelength range and at an intensity configured to be visually perceived by the user as the phototherapeutic light.

In accordance with any of the embodiments disclosed herein, the placebo light is a metameric match of the phototherapeutic light.

In accordance with any of the embodiments disclosed herein, the phototherapeutic light is within a wavelength range that is outside of a visible light spectrum. In accordance with any of the embodiments disclosed herein, the placebo light includes visible light. In accordance with any of the embodiments disclosed herein, the phototherapeutic light includes near-infrared light and the placebo light includes visible light. In accordance with any of the embodiments disclosed herein, the controller includes instructions that, when executed by the controller, cause the phototherapy system to perform operations including emitting the phototherapeutic light and the placebo light during common active periods of time; and not emitting the phototherapeutic light and the placebo light during common inactive periods of time.

This foregoing summary is provided to introduce a selection of concepts in a simplified form that are further described below in the Detailed Description. This summary is not intended to identify key features of the claimed subject matter, nor is it intended to be used as an aid in determining the scope of the claimed subject matter.

Figure 1A:
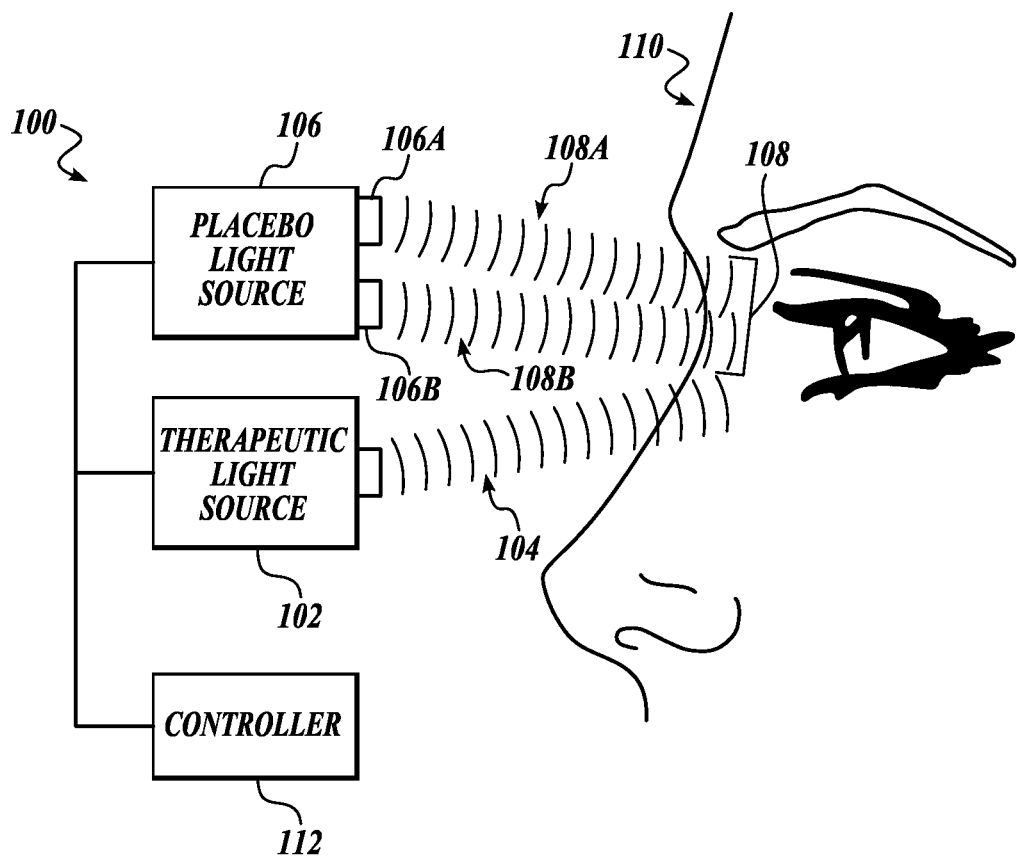
FIG. 1A is a schematic illustration of a phototherapy system, in accordance with an embodiment of the inventive technology.

Aspects and many of the attendant advantages of the claimed subject matter will become more readily appreciated as the same become better understood by reference to the following detailed description, when taken in conjunction with the accompanying drawings.

The detailed description set forth below in connection with the appended drawings, where like numerals reference like elements, is intended as a description of various embodiments of the disclosed subject matter and is not intended to represent the only embodiments. Each embodiment described in this disclosure is provided merely as an example or illustration and should not be construed as preferred or advantageous over other embodiments. The illustrative examples provided herein are not intended to be exhaustive or to limit the claimed subject matter to the precise forms disclosed.

DETAILED DESCRIPTION

The following discussion describes systems and methods for phototherapy. In the examples of systems and methods set forth in more detail below, several are provided that include a therapeutic light source configured to emit phototherapeutic light and a placebo light source configured to emit placebo light. For example, a combination of the phototherapeutic light and the placebo light may be configured to be visually perceived by the subject as continuous light. As used herein, "continuous light" refers to light that does not appear to vary substantially in color and/or intensity over time as visually perceived by a subject, such as a human subject.

Conventional phototherapy can include application of light that stimulates chromophores, for example, in skin of a patient. In some cases, conventional phototherapy includes pulsing such light as it is applied to, for example, skin of the patient. Such pulsing may be uncomfortable or annoying to the patient receiving the phototherapy treatment, particularly, as it is visually received by the patient. Additionally, in some instances, phototherapy includes application of light to the body of a patient that is not visible by human eyes. In this regard, a patient may not know that phototherapy is being performed.

Toward that end, the present disclosure provides phototherapy systems that include a therapeutic light source configured to emit phototherapeutic light towards a subject; and a placebo light source configured to emit placebo light towards the subject. As discussed further herein, such a placebo light source may be configured to emit placebo light that is a metameric match of the phototherapeutic light. In this regard, a subject may not be able to visually distinguish between the phototherapeutic light and the placebo light, thus limiting or preventing a subject's perception of light pulsation. In the following description, specific details are set forth in order to provide a thorough understanding of one or more embodiments of the present disclosure. It will be apparent to one skilled in the art, however, that embodiments of the present disclosure may be practiced without some or all of the specific details. Further, it will be appreciated that embodiments of the present disclosure may employ combinations of features described herein.

Figure 1B:
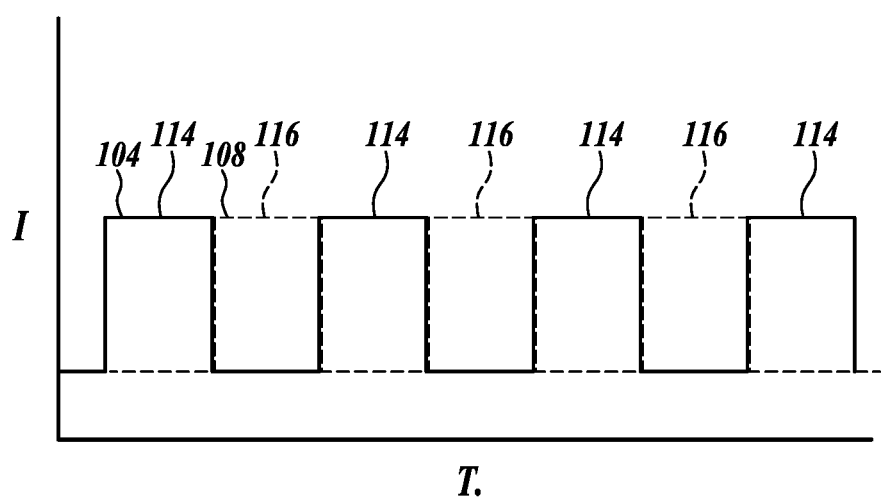
FIG. 1B is a graphic illustration of phototherapeutic light and placebo light generated by a phototherapy system, in accordance with an embodiment of the inventive technology.

Turning now to FIGS. 1A and 1B, there is shown an example of a phototherapy system 100 and light emitted therefrom, in accordance with an embodiment of the disclosure. FIG. 1A is a schematic illustration of the phototherapy system 100. FIG. 1B is a graphic illustration of phototherapeutic light 104 (solid) and placebo light 108 (dashed) generated by the phototherapy system 100.

Illustrated phototherapy system 100 includes a therapeutic light source 102; a placebo light source 106; and a controller 112 operatively coupled to the therapeutic light source 102 and the placebo light source 106. As discussed further herein, the therapeutic light source 102 is configured to emit phototherapeutic light 104 towards a subject 110. As shown in FIG. 1A, phototherapeutic light 104 is emitted from the therapeutic light source 102 towards and, ultimately, onto the subject 110. As used herein, "phototherapeutic light" refers to light 104 that provides or induces a therapeutic benefit to a portion of a subject 110 illuminated by the phototherapeutic light 104. Such therapeutic benefits can include, for example cosmetic benefits to the subject 110, such as benefits including improving an appearance or shape of a portion of the subject 110. Such therapeutic benefits can include treating and/or mitigating causes and/or symptoms of an illness of the subject 110. Such therapeutic benefits can include, for example, an anti-aging effect of the portion of the subject 110 contacted by the phototherapeutic light 104, reducing or removing colored spots, such as freckles, from a portion of the subject 110 contacted by the phototherapeutic light 104, a reduction in frequency and/or severity of acne on a portion of the subject 110 contacted by the phototherapeutic light 104, and the like.

In an embodiment, the phototherapeutic light 104 is configured to be absorbed by and/or stimulate chromophores in the subject 110, such as chromophores disposed in the skin of the subject 110. In an embodiment, the phototherapeutic light 104 includes light having wavelengths in a range of about 400 nm to about 1,200 nm.

As above, the phototherapy system 100 further includes a placebo light source 106. As shown, the placebo light source 106 is configured to emit placebo light 108 towards the subject 110. As used herein, "placebo light" refers to light 108 configured to be visibly perceived by the subject 110, such visibly perceived by the subject 110 as the phototherapeutic light 104. It will be understood by those skilled in the art how to generate placebo light 108 configured to be visually perceived as the same as or similar to the phototherapeutic light 104, whether by spectral color matching, metameric color matching, or the like.

In an embodiment, the placebo light 108 includes light having wavelengths different than those of the phototherapeutic light 104. In an embodiment, the placebo light 108 does not provide the same therapeutic benefits caused or induced by the phototherapeutic light 104, at least in part because the placebo light 108 has different wavelengths than does the phototherapeutic light 104. However, as discussed further herein with respect to FIGS. 2A and 2B, such placebo light 108 may beneficially indicate to the subject 110 that the phototherapeutic light 104 is being applied to the subject 110.

As above, the phototherapy system 100 includes a controller 112 operatively coupled to the placebo light source 106 and the therapeutic light source 102. The controller 112 includes instructions that, when executed by the controller 112, cause the phototherapy system 100 to perform operations. In an embodiment, such operations include emitting the phototherapeutic light 104 from the therapeutic light source 102; and simultaneously emitting the placebo light 108 from the placebo light source 106. While a therapeutic light source 102 for emitting phototherapeutic light 104 and a placebo light source 106 for emitting placebo light 108 is illustrated, it will be understood that a light source configured to emit both phototherapeutic light 104 and placebo light 108 is possible.

In an embodiment, the light emitted by the phototherapy system 100, including the phototherapeutic light 104 and the placebo light 108, is configured to be visually perceived by the subject 110 as continuous light. In an embodiment, the controller 112 includes instructions that, when executed by the controller 112, cause the phototherapy system 100 to perform operations including emitting phototherapeutic light 104 from the therapeutic light source 102 as a plurality of phototherapeutic light pulses 114. An example of such a plurality of phototherapeutic light pulses 114 is illustrated in FIG. 1B. By pulsing the phototherapeutic light 104, therapeutic benefits of the phototherapy may be increased. For example, by pulsing the phototherapeutic light 104, a phototherapeutic light 104 intensity can be increased during the times when the phototherapeutic light 104 is on while reducing unintended or unwanted damage to the portion of the body contacted by the phototherapeutic light 104, because the overall (e.g., time-averaged) effect of the phototherapeutic light 104 is less damaging to the subject 110.

As above, pulsing or flashing light may be annoying and/or uncomfortable to a subject 110 receiving the phototherapy and perceiving the pulsed or flashed phototherapeutic light 104. Toward that end, in an embodiment, the placebo light 108 is emitted in a wavelength range and at an intensity configured to be visually perceived by the subject 110 as or substantially as the phototherapeutic light 104. Further, in an embodiment, the placebo light 108 is a metameric match of the phototherapeutic light 104. In this regard, a subject 110 receiving phototherapy treatment including application of phototherapeutic light 104 may not be able to visually or otherwise distinguish between phototherapeutic light 104 and placebo light 108.

In the illustrated embodiment, the placebo light source 106 includes a first placebo light source 106A configured to emit first placebo light 108A and a second placebo light source 106B configured to emit second placebo light 108B different from the first placebo light 108A. In an embodiment, such first placebo light 108A and second placebo light 108B are suitable to provide the metameric match between the phototherapeutic light 104 and the placebo light 108, particularly where the first placebo light 108A includes light in a first wavelength range and second placebo light 108B includes light in a second wavelength range different from the first wavelength range.

In an embodiment, the controller 112 includes instructions that, when executed by the controller 112, cause the phototherapy system 100 to perform operations including emitting placebo light 108 from the placebo light source 106 as a plurality of placebo light pulses 116. Further, in an embodiment, one or more of the plurality of placebo light pulses 114 are interspersed between phototherapeutic light pulses 114 of the plurality of phototherapeutic light pulses 114. FIG. 1B is a graphic illustration of phototherapeutic light 104 and placebo light 108 generated by a phototherapy system 100. As shown, when the phototherapeutic light 104 cycles off, the placebo light source 106 cycles on to provide placebo light 108. Because the placebo light 108 is perceived by an eye of the subject 110 to be the same as or similar to the phototherapeutic light 104, the subject 110 may not perceive the pulsed nature of the phototherapeutic light 104. Rather, the subject 110 may visually perceive a continuous light emitted by the phototherapy system 100. In this regard, annoyance and/or discomfort associated with pulsed phototherapy is reduced or prevented.

While the plurality of phototherapeutic light pulses 114 and plurality of placebo light pulses 116 are shown as square waves in FIG. 1B, it will be understood that other waveforms are possible. For example, in an embodiment, the controller 112 includes instructions that, when executed by the controller 112, cause the phototherapy system 100 to perform operations including emitting phototherapeutic light 104 from the therapeutic light source 102 as a first sine wave; and emitting placebo light 108 from the placebo light source 106 as a second sine wave out of phase with the first sine wave. Combined light including the first sine wave and the second sine wave may be visually perceptible as continuous light.

Figure 2A:
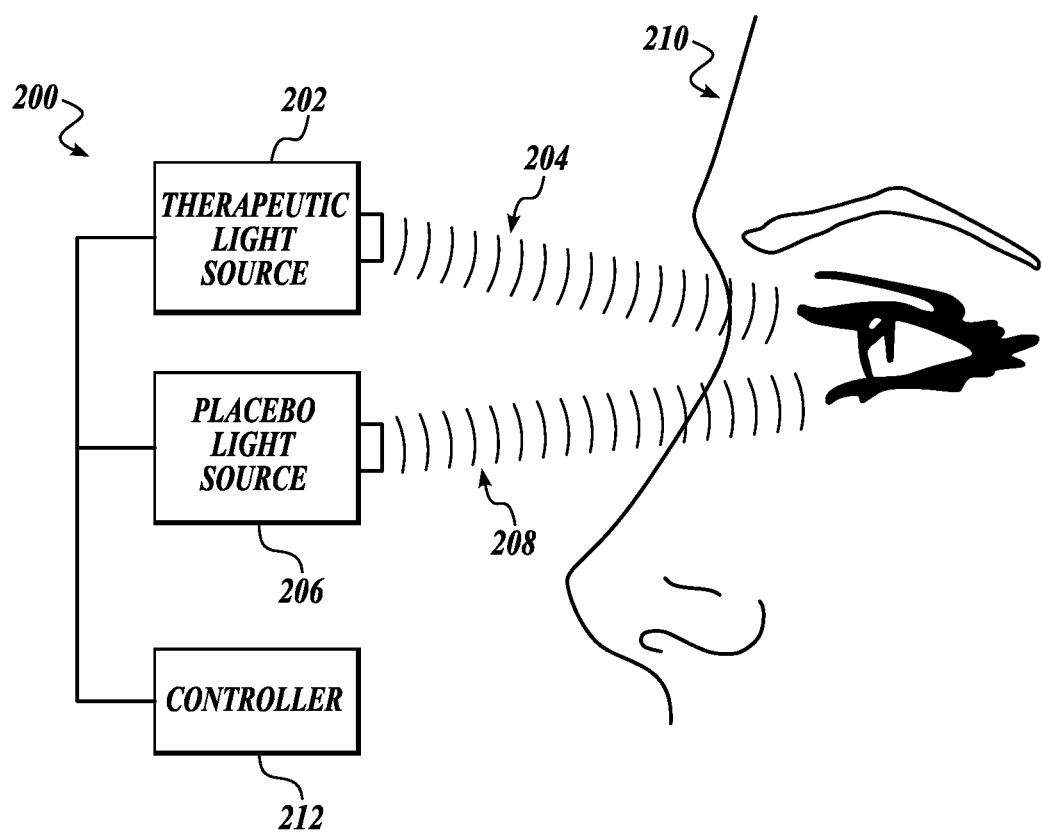
FIG. 2A is a schematic illustration of another phototherapy system, in accordance with an embodiment of the inventive technology.

In an embodiment, the phototherapy systems of the present disclosure are configured to emit phototherapeutic light outside of a visible light range. In that regard, attention is directed to FIG. 2A, illustrating a phototherapy system 200, in accordance with an embodiment of the disclosure. Illustrated phototherapy system 200 is shown to include a therapeutic light source 202 configured to emit phototherapeutic light 204 towards a subject 210; a placebo light source 206 configured to emit placebo light 208 towards the subject 210; and a controller 212 operatively coupled to the therapeutic light source 202 and the placebo light source 206. In an embodiment, the therapeutic light source 202 is configured to emit phototherapeutic light 204 that includes light outside of a visible light spectrum, such as light outside of a range of about 400 nm to about 700 nm. In an embodiment, the phototherapeutic light 204 is entirely outside of a visible light spectrum. In an embodiment, the phototherapeutic light 204 includes near-infrared light and the placebo light 208 includes visible light.

Figure 2B:
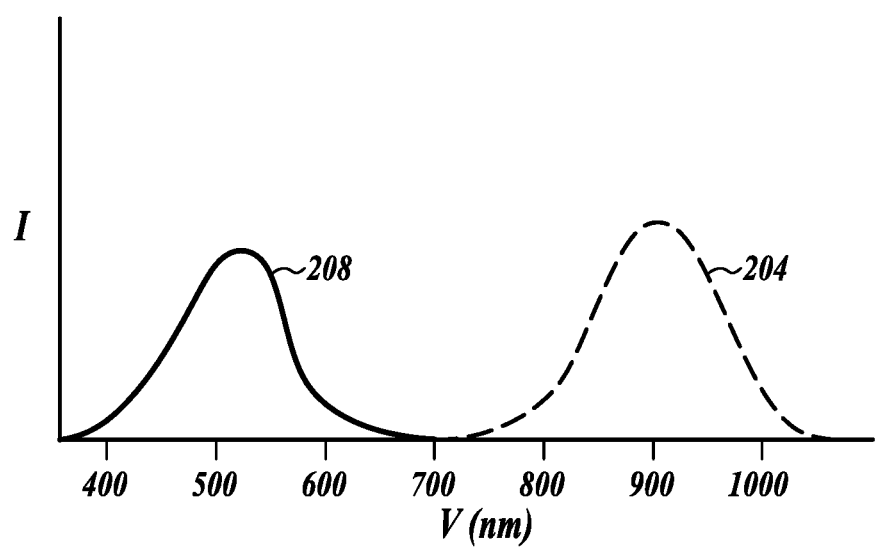
FIG. 2B is a graphic illustration of phototherapeutic light intensity and placebo light intensity as functions of wavelength, in accordance with an embodiment of the inventive technology.

Such phototherapeutic light 204 may not be perceptible by a human eye. In this regard, the subject 210 receiving such phototherapy may not know when the phototherapy is being applied. In an embodiment, the placebo light source 206 is configured to emit placebo light 208 that includes visible light visually perceptible by a human eye. In an embodiment, the placebo light 208 includes light having wavelengths in a range of about 400 nm to about 700 nm. Such placebo light 208 is generally perceptible by human eyes. FIG. 2B is a graphic illustration of phototherapy light intensity and placebo light 208 intensity as a function of wavelength, in accordance with an embodiment of the disclosure. As shown, phototherapeutic light 204 includes light having wavelengths greater than 700 nm and, accordingly, is generally outside of a visible light spectrum and not perceptible by a human eye. In contrast, placebo light 208 is shown to include light having wavelengths between 400 nm and 700 nm and is, thus generally perceptible by a human eye.

Further in an embodiment, the controller 212 includes instructions that, when executed by the controller 212, cause the phototherapy system 200 to perform operations including emitting the phototherapeutic light 204 and the placebo light 208 during common active periods of time; and not emitting the phototherapeutic light 204 and the placebo light 208 during common inactive periods of time. By emitting the phototherapeutic light 204 and the placebo light 208 simultaneously, a subject 210 is provided with a visual indication that the invisible phototherapeutic light 204 is being applied to the subject 210. Such a visual indication is suitable to provide assurance to a subject 210, for example, that the phototherapy is being performed.

In one embodiment, the phototherapy system 200 is configured to provide a number of phototherapies, such as through emission of phototherapeutic light 204 having a number of different wavelength ranges. In an embodiment, the phototherapy system 200 is also configured to emit different placebo light 208 having different placebo light 208 wavelength ranges. Such different placebo light 208 may correspond to the different invisible phototherapeutic light 204. In this regard, the phototherapy system 200 is configured to provide a visual indication that phototherapy is being applied and an indication to the subject 210 of what type of phototherapy is being applied. For example, where the invisible phototherapeutic light 204 provides an anti-aging benefit, the placebo light 208 may be blue. Likewise, where the phototherapeutic light 204 is configured to reduce or eliminate acne, the placebo light 208 may be yellow. When phototherapeutic light 204 has a combined anti-aging and anti-acne effect, the placebo light 208 may be a combination of the yellow and the blue placebo light 208 in the form of green placebo light 208.

In another aspect, the present disclosure provides a method of phototherapy. In an embodiment, the method generally includes emitting phototherapeutic light from a phototherapeutic light source onto a portion of a subject; and emitting placebo light from a placebo light source for visual receipt by the subject. As discussed further herein, combined light including the phototherapeutic light and the placebo light may be configured to be perceived by the subject as continuous light.

Figure 3A:
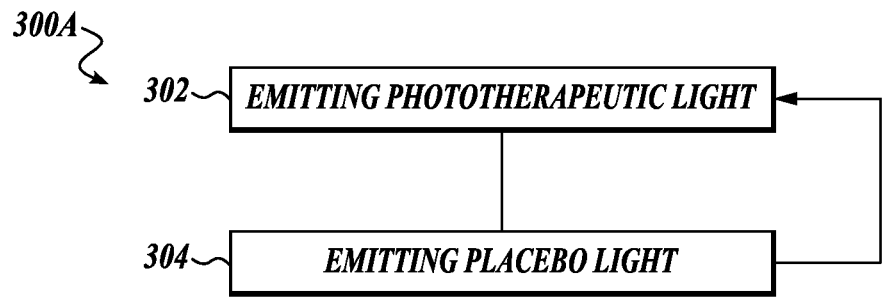
FIG. 3A is a schematic block diagram of a method, in accordance with an embodiment of the inventive technology.

FIG. 3A is a schematic block diagram of a method 300A, in accordance with an embodiment of the disclosure. The method 300A may begin with process block 302, which includes emitting phototherapeutic light. As above, the phototherapeutic light can include light that provides a therapeutic benefit to a portion of the subject contacted by the phototherapeutic light. Process block 302 may be followed by process block 304, which includes emitting placebo light. As discussed further herein, in an embodiment, combined light including the phototherapeutic light and the placebo light is configured to be perceived by the subject as continuous light.

In an embodiment, the method 300A illustrated in FIG. 3A is performed using the phototherapy system 100 illustrated in and discussed further herein with respect to FIGS. 1A and 1B.

As shown, the method 300A may include repeating process block 302 and process block 304 a number of times. In this regard, in an embodiment, the method 300A includes emitting a plurality of phototherapeutic light pulses from the phototherapeutic light source, such as by repeating process block 302 a number of times. Likewise, in an embodiment, the method 300A includes emitting a plurality of placebo light pulses from the placebo light source, such as by repeating process block 304 a number of times.

In an embodiment, one or more of the plurality of placebo light pulses are interspersed between phototherapeutic light pulses of the plurality of phototherapeutic light pulses. As discussed with respect to FIG. 1B, by interspersing one or more of the placebo light pulses of the plurality of placebo light pulses between phototherapeutic light pulses of the plurality of phototherapeutic light pulses, flashing or pulsing of the perceived by the subject may be reduced or eliminated. While square waves of the phototherapeutic light pulses and the placebo light pulses are illustrated in FIG. 1B, it will be understood that other wave forms, such as out-of-phase sine waves, are also possible.

Such a reduction and/or elimination of flashing or pulsing phototherapeutic light is improved especially where emitting the placebo light with the placebo light source includes emitting placebo light in a wavelength range and at an intensity configured to be visually perceived by the user as substantially approximating the phototherapeutic light. For example, when the placebo light is a metameric match, the placebo light and the phototherapeutic light may be imperceptibly different and, in this regard, the subject perceives a continuous combined applied light emitted from the phototherapeutic light source and the placebo light source.

Figure 3B:
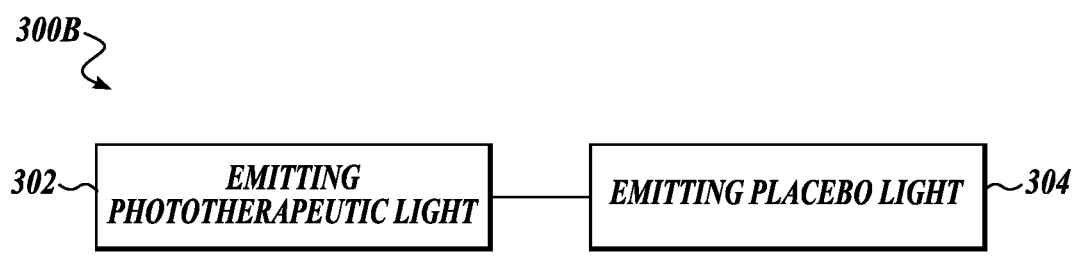
FIG. 3B is a schematic block diagram of another method, in accordance with an embodiment of the inventive technology.

FIG. 3B is a schematic block diagram of another method 300B, in accordance with an embodiment of the disclosure. The illustrated method 300B includes process block 302, which includes emitting phototherapeutic light, and process block 304, which includes emitting placebo light. As shown, process blocks 302 and 304 may be performed simultaneously.

In an embodiment, the method 300B illustrated in FIG. 3B is performed using phototherapy system 200, as illustrated in and discussed further herein with respect to FIGS. 2A and 2B.

In an embodiment, emitting phototherapeutic light in process block 302 includes emitting phototherapeutic light within a wavelength range outside of a visible light spectrum, such as light having wavelengths less than 400 nm and/or greater than 700 nm. In an embodiment, the phototherapeutic light includes near-infrared light and the placebo light includes visible light. As above, phototherapeutic light outside of the visible light spectrum may not be perceptible by a human eye and, in this regard, a subject may not know that the phototherapeutic light is being applied in the absence of additional indicia.

In that regard, in an embodiment, the placebo light includes visible light, such as visible light including light having wavelengths in a range of about 400 nm to about 700 nm, that is visually perceptible by the subject.

As above, in an embodiment, the phototherapeutic light and the placebo light are emitted simultaneously. Accordingly, in an embodiment, emitting the phototherapeutic light and emitting the placebo light includes emitting the phototherapeutic light and the placebo light during common active periods of time; and not emitting the phototherapeutic light and the placebo light during common inactive periods of time.

By emitting the phototherapeutic light and the placebo light during an overlapping period of time, the method 300B provides a visual indication including the placebo light perceptible by the subject that the invisible phototherapeutic light is being emitted and applied to the subject.

It should be noted that for purposes of this disclosure, terminology such as "upper," "lower," "vertical," "horizontal," "inwardly," "outwardly," "inner," "outer," "front," "rear," etc., should be construed as descriptive and not limiting the scope of the claimed subject matter. Further, the use of "including," "comprising," or "having" and variations thereof herein is meant to encompass the items listed thereafter and equivalents thereof as well as additional items. Unless limited otherwise, the terms "connected," "coupled," and "mounted" and variations thereof herein are used broadly and encompass direct and indirect connections, couplings, and mountings. The term "about" means plus or minus 5% of the stated value.

The principles, representative embodiments, and modes of operation of the present disclosure have been described in the foregoing description. However, aspects of the present disclosure which are intended to be protected are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure, as claimed.

While illustrative embodiments have been illustrated and described, it will be appreciated that various changes can be made therein without departing from the spirit and scope of the invention.

The embodiments of the invention in which an exclusive property or privilege is claimed are defined as follows:

1. A phototherapy system comprising:
   a therapeutic light source configured to emit phototherapeutic light towards a subject;
   a placebo light source configured to emit placebo light towards the subject, the placebo light source including a first placebo light source configured to emit first placebo light and a second placebo light source configured to emit second placebo light; and
   a controller operatively coupled to the therapeutic light source and the placebo light source, the controller including instructions that, when executed by the controller, cause the phototherapy system to perform operations including:
  emitting the phototherapeutic light from the therapeutic light source as a plurality of phototherapeutic light pulses; and
  emitting the placebo light from the placebo light source as a plurality of placebo light pulses in a wavelength range that is a metameric match of the phototherapeutic light and at an intensity configured to be visually perceived by the user as the phototherapeutic light,
wherein the phototherapy system is configured to emit light, including the phototherapeutic light and the placebo light, that is configured to be visually perceived by the subject as continuous light,
wherein one or more of the plurality of placebo light pulses are interspersed between phototherapeutic light pulses of the plurality of phototherapeutic light pulses,
wherein emitting the placebo light from the placebo light source includes:
  emitting the first placebo light in a first wavelength range; and
  emitting the second placebo light in a second wavelength range different from the first wavelength range, and
wherein a combination of the first placebo light and the second placebo light provides the metameric match between the phototherapeutic light and the placebo light.

2. The phototherapy system of claim 1, wherein the placebo light includes visible light.

3. The phototherapy system of claim 1, wherein the controller includes instructions that, when executed by the controller, cause the phototherapy system to perform operations including:
  emitting the phototherapeutic light and the placebo light during common active periods of time; and
  not emitting the phototherapeutic light and the placebo light during common inactive periods of time.

4. A method of phototherapy comprising:
  emitting phototherapeutic light including a plurality of phototherapeutic light pulses from a phototherapeutic light source onto a portion of a subject; and
  emitting placebo light including emitting a plurality of placebo light pulses from a placebo light source for visual receipt by the subject, wherein the placebo light is in a wavelength range that is a metameric match of the phototherapeutic light and at an intensity configured to be visually perceived by the user as the phototherapeutic light;
wherein combined light including the phototherapeutic light and the placebo light is configured to be perceived by the subject as continuous light,
wherein one or more of the plurality of placebo light pulses are interspersed between phototherapeutic light pulses of the plurality of phototherapeutic light pulses,
wherein emitting the placebo light from the placebo light source includes:
  emitting first placebo light in a first wavelength range; and
  emitting second placebo light in a second wavelength range different from the first wavelength range, and
wherein a combination of the first placebo light and the second placebo light provides the metameric match between the phototherapeutic light and the placebo light.

5. The method of claim 4, wherein the placebo light includes visible light.

6. The method of claim 4, wherein emitting the phototherapeutic light and emitting the placebo light includes:
  emitting the phototherapeutic light and the placebo light during common active periods of time; and
  not emitting the phototherapeutic light and the placebo light during common inactive periods of time.

* * * * *